(12) United States Patent
Kirnak

(10) Patent No.: US 10,067,995 B2
(45) Date of Patent: Sep. 4, 2018

(54) DATABASE NETWORKS INCLUDING ADVANCED REPLICATION SCHEMES

(76) Inventor: Alean Kirnak, Encinitas, CA (US)

(*) Notice: Subject to any disclaimer, the term of this patent is extended or adjusted under 35 U.S.C. 154(b) by 391 days.

(21) Appl. No.: 11/724,227

(22) Filed: Mar. 15, 2007

(65) Prior Publication Data

US 2007/0185869 A1    Aug. 9, 2007

(51) Int. Cl.
  G16H 10/60    (2018.01)
  G06F 17/30    (2006.01)
  G06F 21/62    (2013.01)
  G06Q 50/24    (2012.01)

(52) U.S. Cl.
  CPC .... G06F 17/30575 (2013.01); G06F 21/6227 (2013.01); G06F 21/6245 (2013.01); G06Q 50/24 (2013.01); G16H 10/60 (2018.01)

(58) Field of Classification Search
  CPC .......................... G16H 10/60; G06F 17/30943
  USPC ................... 705/2–4; 707/201, 100; 283/101
  See application file for complete search history.

(56) References Cited

U.S. PATENT DOCUMENTS

| | | | | |
|---|---|---|---|---|
| 5,504,890 | A | * | 4/1996 | Sanford ............ G06F 17/30554 |
| 5,560,005 | A | | 9/1996 | Hoover et al. |
| 5,664,109 | A | * | 9/1997 | Johnson et al. ................... 705/2 |
| 5,673,944 | A | * | 10/1997 | Walker ................... B42D 5/027 283/101 |
| 5,915,240 | A | * | 6/1999 | Karpf ............................... 705/2 |
| 5,995,980 | A | * | 11/1999 | Olson et al. |
| 6,044,381 | A | * | 3/2000 | Boothby et al. |
| 6,256,634 | B1 | * | 7/2001 | Moshaiov et al. |
| 6,327,611 | B1 | * | 12/2001 | Everingham ................. 709/206 |
| 6,347,322 | B1 | * | 2/2002 | Bogantz et al. |
| 6,347,329 | B1 | | 2/2002 | Evans |
| 6,614,895 | B1 | * | 9/2003 | Impey et al. ............ 379/127.01 |
| 7,047,242 | B1 | * | 5/2006 | Ponte |
| 7,725,428 | B1 | * | 5/2010 | Hawkins et al. |
| 2004/0107256 | A1 | * | 6/2004 | Odenwald et al. ........... 709/205 |

OTHER PUBLICATIONS

Cupito, Mary, "How to find who," Health Management Technology, May 1998, vol. 19, pp. 22-35.*

Thomas, Gomer; Thompson, Glenn R.; Chung, Chin-Wan; Barkmeyer, Edward; Carter, Fred; Templeton, Marjorie; Fox, Stephen; and Hartmen, Berl. "Heterogeneous Distributed Database Systems for Production use." ACM Computing Surveys. vol. 22, No. 3. Sep. 1990. 237-266.

(Continued)

Primary Examiner — John A Pauls

(57) ABSTRACT

To update a database of records having person attributes using an input record containing person attributes and authorization information, a person attribute of an input record is compared to a person attribute for each record in the database, and records in the database are identified as matched records. A composite record is created from the input record and the matched record. A portion of the input record is written to the database if the authorization information contains either an authorized provider ID or a prior-use indicator. An output record is thus generated consisting of the input record and authorization information containing a prior-use indicator. A cascade of a first instance and a second instance wherein the database comprises a first database in the first instance and a second database in the second instance may be performed.

1 Claim, 19 Drawing Sheets

(56) References Cited

OTHER PUBLICATIONS

Donham, Greg W.; and Mallia, Tony. "The Architecture of the FHIE." Journal of AHIMA. Jul.-Aug. 2006. 60-66.
"Application Protocol for Electronic Data Exchange in Healthcare Environments Version 2.5." Jun. 2003. pp. 3-173-3-181, 5-4-5-5, 5-60-5-61.

\* cited by examiner

| Row / Col | 1 | 2 |
|---|---|---|
| | Individual Person | Tier 1 Hub ID |
| 1 | Patient 1 | 1001 |
| 2 | Patient 2 | 1002 |
| 3 | | |
| 4 | Patient 3 | 1003 |
| 5 | | |

*FIG 4*

| Row / Col | 1 | 2 | 3 | 4 |
|---|---|---|---|---|
| | Individual Person | Tier 1 Hub ID | Healthcare Database | Healthcare DB ID |
| 1 | Patient 1 | 1001 | A | 100 |
| 2 | Patient 2 | 1002 | A | 101 |
| 3 | | | B | 100 |
| 4 | Patient 3 | 1003 | A | 102 |
| 5 | | | C | 100 |

*FIG 5*

| Row / Col | 1 | 2 | 3 | 4 | 5 |
|---|---|---|---|---|---|
| | Individual Person | Tier 1 Hub ID | Healthcare Database | Healthcare DB ID | Immunization Status |
| 1 | Patient 1 | 1001 | A | 100 | Up to date |
| 2 | Patient 2 | 1002 | A | 101 | Not up to date |
| 3 | | | B | 100 | Not up to date |
| 4 | Patient 3 | 1003 | A | 102 | Up to date |
| 5 | | | C | 100 | Up to date |

*FIG 6*

| Row / Col | 1 | 2 | 3 | 4 | 5 | 6 |
|---|---|---|---|---|---|---|
| | Individual Person | Tier 2 Hub Person ID | Tier 1 Hub | Tier 1 Hub Person ID | Healthcare Database | Tier 0 Healthcare Database Person ID |
| 1 | Patient 1 | 2001 | X | 1001 | A | 100 |
| 2 | Patient 2 | 2002 | X | 1002 | A | 101 |
| 3 | | | | | B | 100 |
| 4 | | | Y | 1001 | E | 100 |
| 5 | Patient 3 | 2003 | X | 1003 | A | 102 |
| 6 | | | | | C | 100 |
| 7 | Patient 4 | 2004 | Y | 1002 | E | 101 |
| 8 | Patient 5 | 2005 | Y | 1003 | G | 100 |
| 9 | | | | | H | 100 |

FIG 8

| Row/ Col | 1 | 2 | 3 | 4 | 5 | 6 |
|---|---|---|---|---|---|---|
|  | Individual Person | Tier 1 Hub | Tier 1 Hub ID | Other Tier 1 ID | Healthcare Database | Healthcare DB ID |
| 1 | Patient 1 | X | 1001 | none | A | 100 |
| 2 |  |  |  |  | A | 101 |
| 3 | Patient 2 | X | 1002 | 1001 | B | 100 |
| 4 | Patient 2 | Y | 1001 | 1002 | E | 100 |
| 5 |  |  |  |  | A | 102 |
| 6 | Patient 3 | X | 1003 | none | C | 100 |
| 7 | Patient 4 | Y | 1002 | none | E | 101 |
| 8 |  |  |  |  | G | 100 |
| 9 | Patient 5 | Y | 1003 | none | H | 100 |

FIG 10

| Row/ Col | 1 | 3 | 4 | 5 | 6 |
|---|---|---|---|---|---|
|  | Individual Person | Tier 1 X Hub ID | Tier 1 Y Hub ID | Healthcare Database | Healthcare Database ID |
| 1 | Patient 1 | 1001 | none | A | 100 |
| 2 | Patient 2 | 1002 | 1001 | A | 101 |
| 3 |  |  |  | B | 100 |
| 4 | Patient 3 | 1003 | none | A | 102 |
| 5 |  |  |  | C | 100 |

FIG 11

| Row/ Col | 1 | 3 | 4 | 5 | 6 |
|---|---|---|---|---|---|
|  | Individual Person | Tier 1 Y Hub ID | Tier 1 X Hub ID | Healthcare Database | Healthcare DB ID |
| 1 | Patient 2 | 1001 | 1002 | E | 100 |
| 2 | Patient 4 | 1002 | none | E | 101 |
| 3 | Patient 5 | 1003 | none | G | 100 |
| 4 |  |  |  | H | 100 |

FIG 12

|  | Relationship | | Tier | | Queries | | Pushes | |
|---|---|---|---|---|---|---|---|---|
| Relationship X->Y | X | Y | X | Y | X->Y | Y->X | X->Y | Y->X |
| Subset-Superset | subset | superset | N | N+1 | Yes | No | all | common |
| Replicate | replica | replica | N | N | No | No | all | all |
| Peer-to-Peer | peer | peer | N | N | Yes | Yes | common | common |

*FIG 20*

| Database | Connected Database | Relationship (Database -> Connected Database) |
|---|---|---|
| Tier 0 | | |
| A | X | Subset |
| B | X | Subset |
| C | X | Subset |
| D | Z | Peer-to-Peer |
| E | Y | Subset |
| F | Y | Subset |
| G | Y | Subset |
| H | Y | Subset |
| Tier 1 | | |
| X | A | Superset |
| X | B | Superset |
| X | C | Superset |
| X | D | Superset |
| X | Z | Subset |
| W | Z | Subset |
| Y | E | Superset |
| Y | F | Superset |
| Y | G | Superset |
| Y | H | Superset |
| Y | Z | Subset |
| Tier 2 | | |
| Z | X | Superset |
| Z | W | Superset |
| Z | Y | Superset |
| Z | D | Peer-to-Peer |
| Z | ZZ | Replicate |
| ZZ | Z | Replicate |

FIG 22

DATABASE NETWORKS INCLUDING ADVANCED REPLICATION SCHEMES

CROSS-REFERENCE TO RELATED APPLICATIONS

This application is a continuation-in-part of U.S. patent application Ser. No. 11/042,904, filed Jan. 25, 2005, which itself is a continuation of U.S. patent application Ser. No. 09/561,745, filed Apr. 28, 2000, which itself claims the benefit of U.S. Provisional Patent Application No. 60/131,434, filed Apr. 28, 1999. Further, this application claims the benefit of U.S. Provisional Patent Application No. 60/783,008, filed Mar. 15, 2006, and now pending. The contents of these U.S. patent application Ser. Nos. 11/042,904, 09/561,745, 60/131,434, and 60/783,008, are all hereby incorporated by reference in their entirety.

BACKGROUND OF THE INVENTION

Field of the Invention

The present application relates to medical records, and specifically, to a method, system, and apparatus for sharing medical records among a set of disparate healthcare databases.

Related Art

Development has been underway for years to connect disparate healthcare systems to provide access to a complete medical history for a patient. Such efforts are known as "healthcare interoperability" or "interoperable health IT" (see www.hhs.gov/healthit/). A number of architectural approaches have been proposed, discussed and piloted, but there is not yet any single model that has gained wide acceptance and success.

A model is needed to provide automatic, ongoing updates to a Hub from Provider healthcare systems within the context of a fully functional healthcare interoperability project.

SUMMARY OF THE INVENTION

The invention disclosed here provides an apparatus that initializes and updates Domains, according to a wide variety of possible configurations. One or more instances of the invention, along with any Hubs required by the desired configuration, are added to existing legacy healthcare systems. The operation of the invention thus facilitates the building and maintenance of a network for healthcare information exchange. The invention was created to allow for automatic, ongoing updates to a Hub from Provider healthcare systems within the context of a fully functional healthcare interoperability project. This can only be accomplished if correctness of the data is guaranteed to be maintained.

Accordingly, in some embodiments, a method is disclosed for updating a database of records having person attributes using an input record containing person attributes and authorization information, wherein the database is associated with a set of authorized provider IDs and wherein each record of the database has a unique provider ID and wherein the authorization information contains either a unique provider ID or a prior-use indicator. The method comprises the steps of comparing a person attribute of the input record to a person attribute for each record in the database and identifying a record in the database as a matched record upon a match therebetween; creating a composite record from the input record and the matched record; writing at least a portion of the input record to the database if the authorization information contains either an authorized provider ID or a prior-use indicator; and generating an output record wherein the output record consists of the input record and wherein the authorization information of the output record contains a prior-use indicator.

In some embodiments, an apparatus is disclosed which implements Notifications, constrained by a mechanism (a Filter) for enforcing the Single Source Rule.

In some embodiments, by implementing the Single Source Rule and its concomitant Transactional Integrity Rule, Provider control over its own data is maintained. This feature may be seen as a prerequisite to Provider participation in healthcare interoperability, given Provider fiduciary responsibilities toward their patients, as well as liability, competitive, and privacy concerns, and more.

In some embodiments, a Display design is disclosed which supports the enforcement of the Single Source Rule.

In some embodiments, Queries are disclosed which provide for greater flexibility in configuring Domains and providing for additional functionality within healthcare interoperability systems. Queries enable Medical Records to be retrieved from higher-Tier Domains upon demand, and reduce the need to store data locally, or re-enter it.

In some embodiments, Medical Records belonging to the same Individual Person may be matched.

In some embodiments, a mechanism is disclosed for assigning Person Identifiers. It may support various Domains configurations, including Tiers, and superset, subset and peer-to-peer relationships among Databases.

In some embodiments, various mechanisms are provided for filtering data. These include recording the source location of data, screening certain data fields from sharing or display, and processing data in various fashions as passes through the apparatus.

In some embodiments, cascading is provided. This feature allows it to be used repeatedly to create a widespread and complex network of healthcare interoperability.

It will be clear to one skilled in the art that the disclosed methods may be implemented in many ways. As non-limiting examples, the databases may be maintained on physical storage devices on one or more servers at different physical locations which can communicate with each other or with a central control microprocessor by TCP/IP or any known network protocol. The same or a different network protocol may also be used for communication between any such control microprocessor and a display recipient or data modifier, or with another server. Alternately, databases may be maintained on a single system (for example, in an intranet environment), where the system also interacts directly with the users. Interfaces may be provided in HTML, in PHP pages, in XML format, in JAVA formats, or in any other appropriate format. SQL, MySQL, Oracle or any such equivalent database format may be used. The database can be embodied, read and written to in other ways known to those skilled in the art; these are only examples.

BRIEF DESCRIPTION OF THE DRAWINGS

FIG. 4 depicts Person Identifiers Associated with a Tier in accordance with the invention.

FIG. 5 depicts Person Identifiers in a Two-Tiered Domain in accordance with the invention.

FIG. 6 depicts a Set of Patient Views Contained in a Hub of a Two-Tiered Domain in accordance with the invention.

FIG. 8 depicts a Master Person Index for a Multi-Tiered Domain in accordance with the invention.

FIG. 10 depicts Person Identifiers in a Peer-to-Peer Domain in accordance with the invention.

FIG. 11 depicts a Master Person Index for Tier 1 X Hub of Peer-to-Peer Relationship in accordance with the invention.

FIG. 12 depicts a Master Person Index for Tier 1 Y Hub of Peer-to-Peer Relationship in accordance with the invention.

FIG. 20 depicts Subset-Superset Relationships, Replicate Relationships, and Peer-to-Peer Relationships in accordance with the invention.

FIG. 22 depicts an example of Relationships Among Databases in accordance with the invention.

DETAILED DESCRIPTION

Overview

Figure 1:
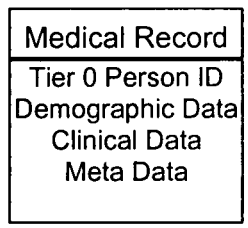
FIG. 1 depicts a Trivial Case of a Patient View in accordance with the invention.

An apparatus is disclosed for sharing medical records among a set of disparate healthcare databases. The invention provides a cascadable apparatus, one instance of which is connected with each healthcare database. The operation of the apparatus produces a healthcare information network in which all medical records for any individual person can be accessed without compromising control of those records by the provider who generated them.

The invention takes the approach of controlling the ability to add, update or delete data. The ability to read or view data, on the other hand, may be shared, within configurable limits.

The invention is built around a body of database computer science theory that is easily understood by anyone with ordinary skill in the art. It keys off of data replication theory, since, practically speaking, all healthcare interoperability projects involve some sort of data replication, even if it is restricted to the replication of demographic data for purposes of building a Master Person Index (MPI). By respecting the design principles of data replication models, the invention ensures that the data sharing actions of healthcare interoperability maintain correctness of the demographic and clinical data presented.

The apparatus may be disposed as a library of software modules which can be used at the core of a single interoperability application, or which can be installed repeatedly across a set of heterogeneous applications and connected to each other to create a flexible topology over a network of interoperable healthcare systems.

The invention may alternatively be disposed as an N-tier, web-based application which serves as an out-of-the-box complete healthcare interoperability application, demonstrating the full functionality of the invention.

For clarity, a framework of definitions and an architectural model bearing similarities to that described in Donham et. al. will now be described. The following definitions are intended to be non-limiting, and are provided only to facilitate review of the specification.

As used herein, the term "Storage Medium" may refer to any physical medium for storing a database, including RAM memory, flash memory, ROM memory, EPROM memory, EEPROM memory, registers, hard disk, a removable disk, a CD-ROM, or any other form of storage medium known in the art. A storage medium may be coupled to a processor such that the processor may read information from, and write information to, the storage medium.

As used herein, the term "Individual Person" may refer to an actual person (as opposed to a computer record associated with a person).

As used herein, the term "Person Identifier" may refer to a unique identifier indicating an Individual Person.

As used herein, the term "Demographic Data" may refer to data describing an Individual Person, such as his name, date of birth, address, and so forth.

As used herein, the term "Clinical Data" may refer to data describing an Individual Person's medical history or medical condition, such as his lab test results, medication history, immunization history, and so forth.

As used herein, the term "Meta Data" may refer to other data that is derived from Demographic Data and Clinical Data for an Individual Person, such as the location of Clinical Data, decision support data, disclosure/consent status, and so forth.

As used herein, the term "Medical Data" may refer to any combination of Demographic Data, Clinical Data and Meta Data.

As used herein, the term "Location Data" may refer to a special case of Meta Data that indicates the location of an Individual Person's data across zero or more Databases.

As used herein, the term "Provider" may refer to an entity that controls particular Medical Data. These Medical Data are said to be "associated with" the particular Provider.

As used herein, the term "User" may refer to an Individual Person associated with a Provider who can edit and view certain Medical Data associated with that Provider.

A Provider is usually an organization, with many Users associated with it. In the trivial case, a Provider can be associated with a single Individual Person. This feature allows accommodation of the consumer or patient who wishes to access his own Personal Health Record (PHR).

As used herein, the term "Medical Record" may refer to the Person Identifier and Medical Data generated by a Provider for an Individual Person.

As used herein, the term "Patient View" may refer to a recursive assembly of one or more Medical Records and Patient Views, plus a Person Identifier. A single Medical Record is the trivial case of a Patient View.

As used herein, the term "Matching Algorithm" may refer to a computer software module that determines that two or more Patient Views are in fact associated with the same Individual Person and can be assembled (or "merged") to create a single Patient View.

As used herein, the term "Database" may refer to a set of Patient Views, possibly in a persistent data store (such as hard disks, etc.) A database is a computer organization of data in which a unique identifier is assigned to each row in each table. In this discussion, the entire software application including the database may be referred to as a Database, even though software applications may include much more than a "database"—i.e. graphical user interfaces, application servers, etc., and these too are part of the term "Database" as used herein.

As used herein, the term "Provider View" may refer to the set of all Patient Views in a Database associated with a particular Provider.

As used herein, the term "Hub" may refer to a Database that stores a plurality of Provider Views.

As used herein, the term "Master Person Index (MPI)" may refer to the Person Identifier and Demographic Data portions of a Hub.

As used herein, the term "Display" may refer to any computer workstation, handheld device, terminal, etc. that allows a User to view and edit Patient Views.

As used herein, the term "Service" may refer to a software program that is made available for use by other software programs through a defined interface.

As used herein, the term "Query" may refer to an atomic (completed all or none) sequence of Services that retrieves a Patient View from a Database.

As used herein, the term "Notification" may refer to an atomic (completed either all or none) sequence of Services that sends a Patient View unsolicited from one Database to another. Also called a "Push".

As used herein, the term "Issue Query" may refer to a Service that initiates a Query.

As used herein, the term "Accept Query" may refer to a Service that accepts and processes an Issue Query.

As used herein, the term "Issue Response" may refer to a Service that responds to an Accept Query.

As used herein, the term "Accept Response" may refer to a Service that accepts and processes an Issue Response.

As used herein, the term "Issue Push" may refer to a Service that initiates a Notification.

As used herein, the term "Accept Push" may refer to a Service that accepts and processes an Issue Notification.

As used herein, the term "Issue Ack" may refer to a Service that responds to an Accept Notification.

As used herein, the term "Accept Ack" may refer to a Service that accepts and processes an Issue Ack.

As used herein, the term "Filter" may refer to a Service that processes a Patient View in some way, often producing Meta Data as output.

As used herein, the term "Domain" may refer to a network of interconnected Databases in which a path exists (by one or more links) from each Database to every other Database.

As used herein, the term "Subdomain" may refer to a subset of a Domain which is in itself a Domain.

As used herein, the term "Tier" may refer to a layer of assembly of Patient Views in which an additional stream of Person Identifiers is necessitated or implied.

As used herein, the term "Data Replication" may refer to an activity that causes data such as a Patient View to be copied from one Database to another.

As used herein, the term "Single Source Rule" may refer to a design principle of Data Replication that states that, for any row-column subset of data, one and only one copy within the Domain is editable, and the rest are view-only replicas. The editable copy is referred to as the Single Source.

As used herein, the term "Transactional Integrity Rule" may refer to a design principle of Data Replication which states that all adds, updates, and deletes applied at the Single Source are to be effectively applied in order to all other replicas.

Patient View

The Patient View, defined above, is an abstraction which provides the foundational data structure representing the heterogeneous systems found throughout the healthcare economy. The Patient View is consistent with typical clinical data models. Clinical data models include, for example, the Continuity of Care Document (CCD) published by the American Society for Testing and Materials (ASTM) and Health Level 7 (HL7); and data models supported by Electronic Medical Record (EMR) systems.

Figure 2:
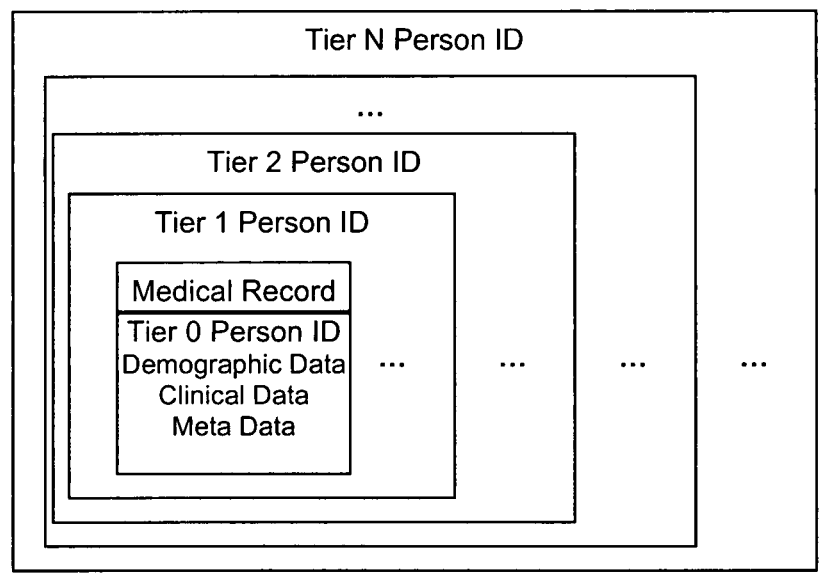
FIG. 2 depicts a Multi-Tiered Patient View in accordance with the invention.

A Patient View may contain just one Medical Record, as depicted in FIG. 1. As Medical Records are shared, a multi-Tiered Patient View, depicted in FIG. 2, may be aggregated. Such a Patient View is recursively built by associating existing Patient Views with each other and linking them with Person Identifiers from using successive identifier streams.

Structure

An example of the underlying structure of an embodiment of the invention will now be described with reference to FIGS. 1-12.

Domains and Tiers

Domains and Tiers will now be illustrated with reference to FIGS. 1-6.

Healthcare interoperability implies a network of interconnected Databases. The set of interconnected Databases may be referred to as a "Domain." To share data, communication should exist, at least temporarily, between each Database and every other Database in the network. The path between any pair of Databases can be via a single communication link or a series of links. In the trivial case, a Domain contains a single Database and no connections.

A "Tier" is a level of aggregation of Patient Views in which a new system of Person Identifiers is required. For each Tier, some mechanism assigns the new Person Identifiers. In the trivial case, a Database contains a single system of Person Identifiers, as in the case of a Database containing Medical Records. Indexing Tiers to 0, the trivial case is referred to as a "Tier 0 Database".

In multi-Tiered Domains, the new Person Identifiers may be stored in a Hub. The new Person Identifiers plus their mappings to Person Identifiers of connected Databases is referred to as a Master Person Index (MPI). Such a Hub may or may not also store other portions of Patient Views, such as Clinical Data.

In the example of the MPI, in order to aggregate the Demographic Data necessary for building the Hub, connections must be established between the Hub and the Databases in the Domain. A Two-Tiered Domain might contain a single Hub connected to several healthcare Databases, as illustrated in FIG. 3.

Figure 3:
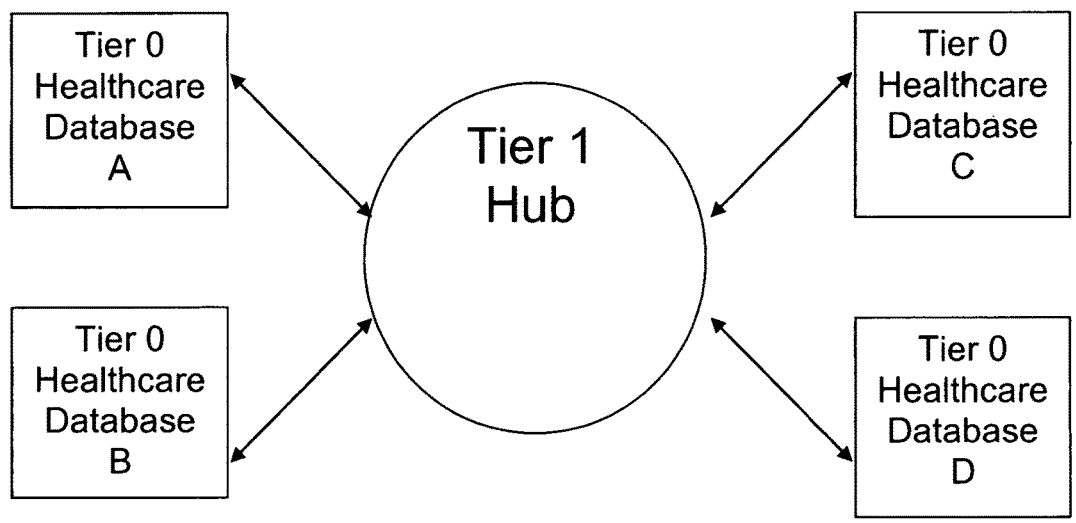
FIG. 3 depicts a Two-Tiered Domain in accordance with the invention.

The Person Identifiers of the Tier 1 Hub of FIG. 3 are illustrated in FIG. 4. Column 2, "Tier 1 Hub ID", is the new system of Person Identifiers.

FIG. 5 also illustrates the Person Identifiers associated the Tier 1 Hub of FIG. 3, but includes the mapping of the Tier 1 Person Identifiers to the Person Identifiers of the Tier 0 Databases of the Domain. The association of Columns 3 and 4 to Column 2 gives the mapping of Tier 1 Person Identifiers to Tier 0 Person Identifiers.

Observe that FIG. 6 illustrates a Master Person Index, or MPI. Note that FIG. 5 also includes some Location Data, as it indicates the source of the Person Identifier in Column 3. Finally, note that while Column 2 uniquely identifies an Individual Person, the combination of Columns 3 and 4 also identify an Individual Person. It is an artifact of MPIs that a combination of the source Database, as in column 3, and the unique Person Identifier within that Database, as in column 4, also uniquely identifies an Individual Person. However, for a variety of reasons not discussed here, a new system of Person Identifiers, as in Column 2, is usually created as well.

For each Tier, some mechanism, such as a Service, must assign the associated Person Identifiers.

FIG. 5 can also be extended to include other data such as Clinical Data. This is given in FIG. 6. Although FIG. 4 through FIG. 6 each illustrates a set of Patient Views, FIG. 4 and FIG. 5 contain smaller subsets of each Patient View, and FIG. 6 contains a more complete set of the Medical Data within each Patient View.

Building Domains

The model of Tiers and Domains may be extensible to additional Tiers, as will now be illustrated with reference to FIGS. 7-12.

Figure 7:
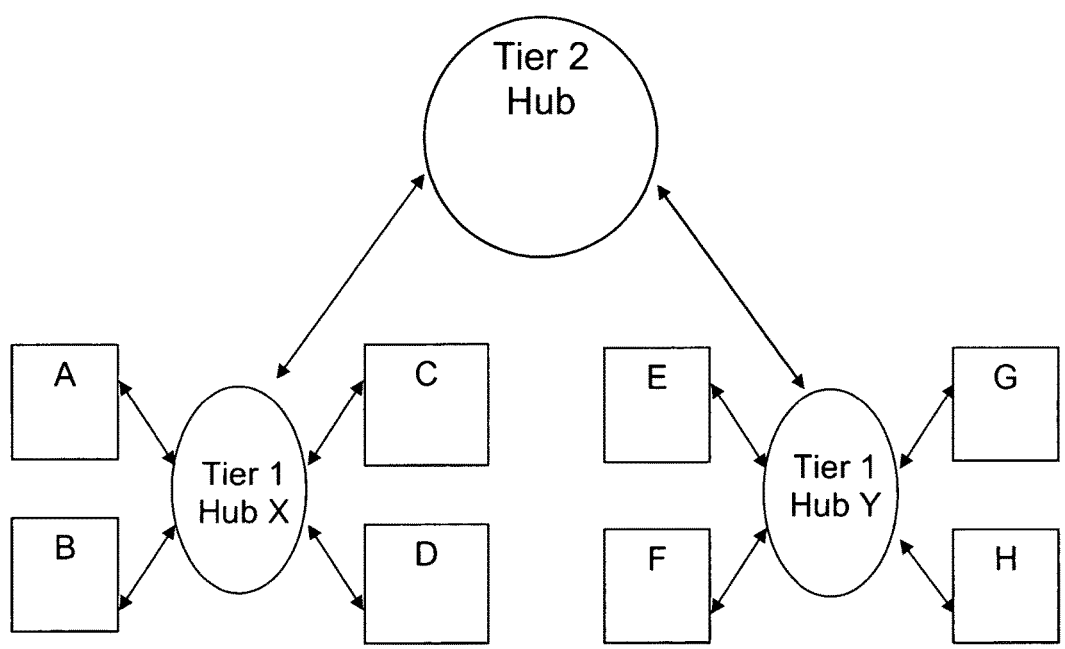
FIG. 7 depicts a Multi-Tiered Domain in accordance with the invention.

A Multi-Tiered Domain is illustrated in FIG. 7. FIG. 8 shows the Person Identifiers of the Tier 2 Hub of FIG. 7. Note a match between a Patient View of Tier 1 Hub X and a Patient View of Tier 1 Hub Y is reflected in the association of Rows 2 and 3 with Row 4 for Patient 2.

The Tiers of Person Identifiers are reflected on a macro level in the architecture of the Domain, and in the micro level in the Patient View.

A Domain may also be a combination of Domains. The key is that a connection exists from any Database in the Domain to any other. A subset of a Domain, such as that illustrated by A, B, C, D, and Tier 1 X in FIG. 7, is called a "Subdomain."

Multi-Tiered Domains contain Single-Tiered Subdomains. The relationship between the each Tier 1 Hub and the Tier 2 Hub of FIG. 7 is a Subset-Superset relationship. The Tier 2 Hub contains all the Patient Views of each Tier 1 Hub, but neither Tier 1 Hub is required to contain all the Patient Views of the Tier 2 Hub.

Databases in two Subdomains may also be related by a Peer-to-Peer relationship. A Peer-to-Peer relationship is one in which the Person Identifiers of each Database are mapped to the Person Identifiers of the other. Peer-to-peer Databases have either an "intersection" or "replicate" relationship with each other. In an intersection relationship, a subset of the Patient Views in one Database are also a subset of the Patient Views in the other. In a replicate relationship, each Database contains all the Patient Views of the other. Peer-to-Peer Hubs have what is also known as a "point-to-point" relationship.

Figure 9:
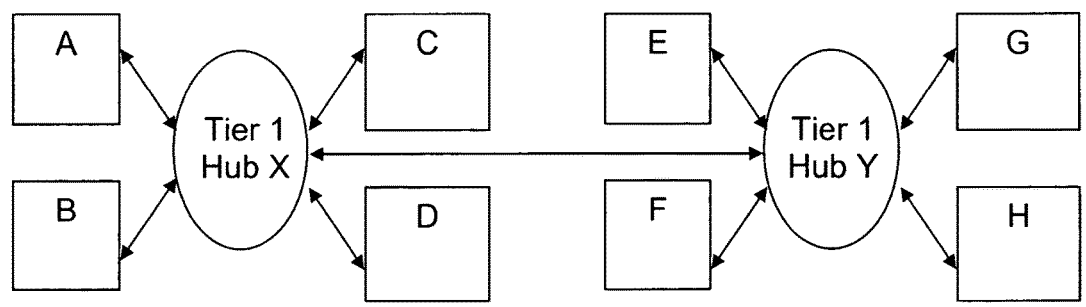
FIG. 9 depicts a Peer-to-Peer Relationship Between Hubs in accordance with the invention.

FIG. 8 show a configuration without the Tier 2 Hub of FIG. 7. The MPIs of each of the Tier 1 Hubs of the Peer-to-Peer relationship of FIG. 9 are illustrated in detail in FIG. 11 and FIG. 12. FIG. 10 depicts Person Identifiers in a Peer-to-Peer Domain in accordance with the invention.

Note that while each of X and Y contains Person Identifiers for all of the Individual Persons whose Patient Views are stored within its Subdomain, neither has a complete set for the entire Domain. Thus, no single column contains a Person Identifier for each Individual Person in the Domain. If such a system of Person Identifiers is required, the Domain can be reconfigured to appear more like FIG. 7: two Hubs in a Peer-to-Peer relationship are interchangeable with two Hubs, each in a common Subset-Superset relationship with a higher-Tier Hub. Peer-to-Peer relationships are useful among small numbers of Databases, such as between a Hub and a Database used for analysis purposes, or between two Databases in a small Domain. In larger Domains, the use of higher-Tier Hubs shortens long chains of Peer-to-Peer relationships and minimizes the total number of connections, improving the performance of operations such as Queries and Notifications.

Operation

An example operation of an embodiment of the invention will now be described with reference to FIG. 13. Note that in this and other embodiments, the invention may include a set of services that can be externally exposed, such as through web services. For example, the invention may be packaged for offering as part of a service-oriented architecture (SOA) or other modular approach.

Figure 13:
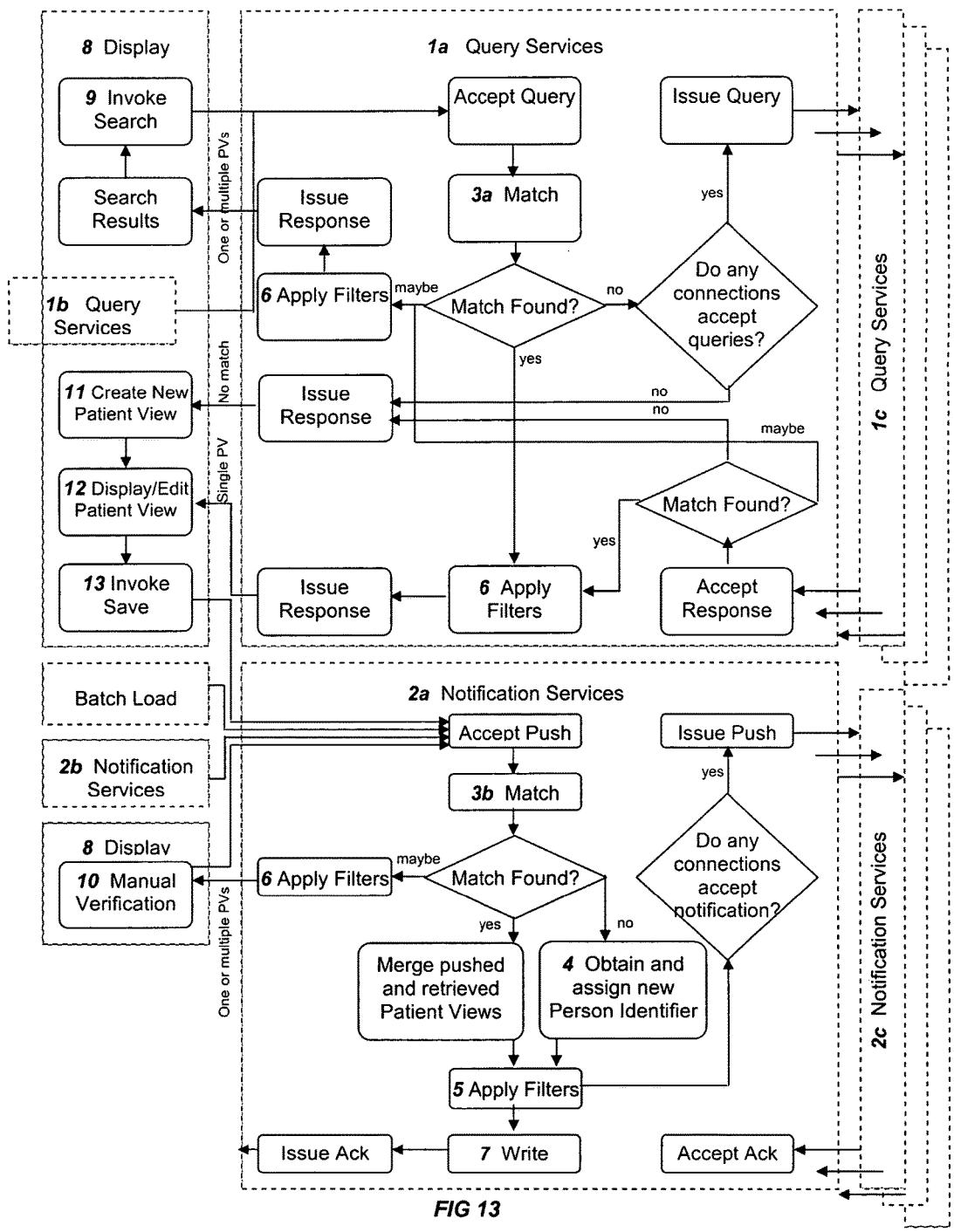
FIG. 13 charts the operation of an embodiment in accordance with the invention.

Making reference to FIG. 13, the dotted-line boxes labeled "1a Query Services" and "2a Notification Services" together represent a single instance or occurrence of the apparatus. In its present embodiment, both "1a Query Services" and "2a Notification Services" and all supporting Services are present. However, only "2a Notification Services" is required for a minimum embodiment.

Query services 1a includes
Issue Query
Accept Query
Issue Response
Accept Response
Notification services 2a includes:
Issue Push
Accept Push
Issue Ack (Issue Push Acknowledgement)
Accept Ack (Accept Push Acknowledgement)
Services that support 1a and 2a include:
A Matching Algorithm 3a and 3b.
Mechanisms for issuing Person Identifiers 4.
A filter 5 that enforces the Single Source Rule.
Other filters 6 such as data location filters, confidentiality filters, decision support filters, etc.
Services that read and write 7 Patient Views to and from a Database.

The user interface Display 8 provides certain Services to users who enter and edit data. These Services include:
Invoke a search 9 for a Patient View.
Manually verification 10 of a record match.
Create a new Patient View 11.
Display a Patient View 12 to a user.
Accept Patient View 12 edit actions from a user.
Accept a "save Patient View" 13 action from a user.

The above services, however, are all non-limiting examples, and the full scope of the invention is independent of any particular implementation of any Service. For example, the invention supports different Patient View models, interfaces to different relational databases, different Matching Algorithms, different Filters etc. Likewise, the Display may be built to perform the above functions, be adapted from an existing Electronic Medical Record (EMR) or other legacy application, etc.

Database Reads and Writes

Database reads are done during the course of the Matching Algorithm 3a and 3b in Query Services 1a and Notification Services 2a respectively. Writes 7 are done in the course of Notification Services 2a. The read and write Services are performed on Databases associated with the apparatus of FIG. 13.

In the present embodiment, each instance of Query Services 1a and Notification Services 2a is associated one Database. In another embodiment, the apparatus may be associated with more than one Database. Such Databases may be replicas of each other, produced for performance or fault tolerance reasons, or they may be parallel arrays of Databases.

Data Replication

Notification Services 2a implements Data Replication. In this discussion, Data Replication consists in copying a Patient View or portion thereof from one Database to another. For example, when a Hub is created with a MPI, Patient Views originating at Provider Databases are replicated to the Hub, at least in part (i.e., the Person Identifiers and the Demographic Data), through the Issue Push and Accept Push Services. Usually, Data Replication is thought of as associated with Notification Services rather than Query Services. In this invention, however, Data Replication is also an effect of executing Issue Query and Accept Response Services, followed by an Issue Push of the results into a local Database.

Two principles, which are by way of this disclose believed to be clear to one ordinarily skilled in the art, ensure correctness in a system of Data Replication.

1. Single Source Rule: for any row-column subset of data, one and only one copy within the Domain is editable, and the rest are view-only replicas. For purposes of this discussion, this copy is called the Single Source.
2. Transactional Integrity Rule: All adds, updates, and deletes applied at the Single Source are applied in order to all other replicas.

The "in order" part of Transactional Integrity Rule is more important than the fact that the updates are applied. If updates are not applied at all to replicas, then the replicas will be out of date with respect to the original. However, if transactions are applied out of order, or if the Single Source Rule is not respected, then the replica could actually be incorrect with respect to the original.

It is thus important that correctness be maintained in any interoperability solutions involving Data Replication. The invention implements the Single Source Rule through the use of an Edit Rules Filters. The Transactional Integrity Rule is enforced through the apparatus design.

Filters

Note the use of Filters in FIG. 13. A Filter is any type of processing that is done on a Patient View, taking advantage of the fact that Medical Records from various Providers for one Individual Person have been assembled. A Filter may produce output in the form of Meta Data. A patient locator may be considered a form of filtering, as it produces Meta Data indicating that one portion of the Clinical Data for an Individual Person resides in one location and another portion elsewhere.

Other Filters include:

Disclosure/consent, which gives information about the Individual Person's knowledge that his Medical Records are being shared, and his permission to share them;

Decision support, which applies clinical rules to the Patient View and aid Users in making clinical decisions. A Vaccine Forecast Module (VFM), which predicts the next immunizations due based upon Advisory Committee on Immunization Practices (ACIP) rules, is an example of a decision support Filter.

Data validation. A Filter that reviews an immunization history, marks all the vaccines as valid or invalid according to clinical rules, and numbers doses, is an example.

Semantic interoperability. Formatting the various Medical Records in a Patient View to use common data definition tables, such as LOINC or SNOMED codes, is an example.

Edit Rules filter. The Edit Rules Filter is a unique and essential feature of the invention. It enforces Provider control over the editing of its own data, and allows the invention to operate without introducing correctness errors into Patient Views as they are updated from multiple Provider sources.

Edit Rules Filter

Notification Services 2a contains an Edit Rules Filter. The Edit Rules Filter enforces the Single Source rule of Data Replication. The edit rules Filter restricts the editing of any Medical Record portion of a Patient View to Users of the Provider associated with it. Each Issue Push Service carries information about the Provider who invoked it. This information is passed from Notification Services 2a to Notification Services 2c, and so forth, as the Notification Services are cascaded.

Notification Services 2a queues any subsequent Push messages in stable storage. By doing this as part of the atomic Notification Services process, and by properly handling errors and failures, the invention may ensure that edits are cascaded throughout the Domain in the order they occur.

Through the integrity of the Notification Services, the invention may conform to the Transactional Integrity Rule.

Display

A user interface Display 8 is also depicted in FIG. 13.

The user interface Display may be designed to respect the edit rules enforced by the Edit Rules Filter. It may thus permit Users to edit only those portions of the Patient View associated with the same Provider the Users are associated with.

Figure 14:
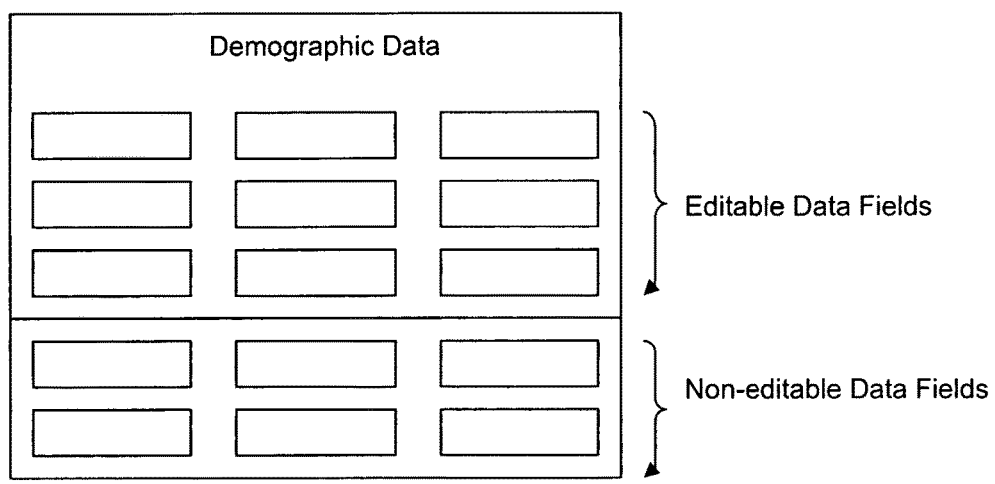
FIG. 14 depicts an Example Display Screen in accordance with the Invention.
Figure 15:
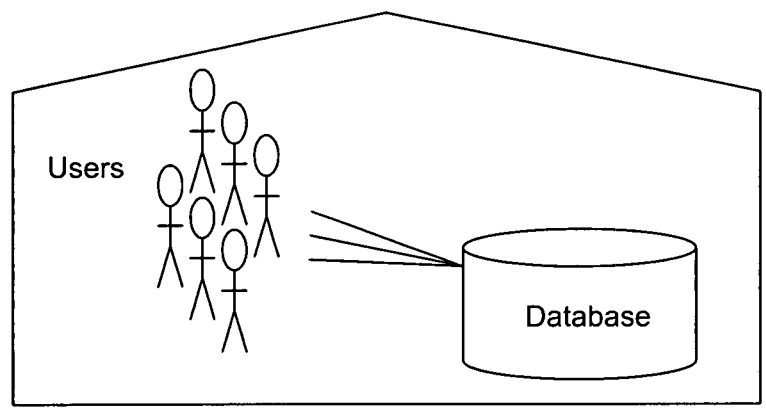
FIG. 15 depicts an example of Providers, Users, and Databases in accordance with the invention.

An example Display is further depicted in FIG. 14. In the example, a top portion of a user screen displays Demographic Data generated by the Provider associated with the User's login, while Demographic Data generated by other Providers is displayed in the lower half of the screen. The top half of the screen allows editing, while the bottom half does not.

In some embodiments, confidentiality filters may also be applied in this fashion. For example, some data fields may be masked for portions of the Patient View associated with other Providers, while the equivalent data fields are visible for portions of the Patient View associated with the User's Provider.

Note the manual verification function 10 of FIG. 13. The Manual Verification 10 allows a User to consider a Patient View and manually select from a list of potentially matching Patient Views as returned by the Matching Algorithm 3a. This occurs if and when Matching Algorithm 3a is unable to make a determination automatically, usually a small percentage of the time. The Manual Verification 10 may be performed in one embodiment by an operator reviewing indeterminate matches resulting from a batch load of Patient Views.

Ability to Cascade

Note that the Query Services 1a and Notification Services 2a of FIG. 13 can be cascaded.

FIG. 13 shows that the Query Services 1a activated by an Issue Query service invoked by another instance of Query Services, 1b. Likewise, a path through the logic of 1a results in one or more invocations of Issue Query, received by the corresponding Accept Query of one or more instances of Query Services 1c.

Likewise, a path through the logic FIG. 13 shows the Notification Services 2a activated by an Issue Push invoked by another instance of Notification Services, 2b. A path through the logic of 2a results in one or more invocations of Issue Push, received by the corresponding Accept Push of one or more instances of Notification Services 2c.

The ability to cascade is an important feature of the invention that allows for the flexible configuration of Domains.

Configuration

Each instance of the invention may be configured to specify its connection and type of relationship with:
Databases.
User interfaces displays.
Other instances of the invention.
Other configurable aspects such as the Service that issues Person Identifiers.

The configuration of instances of the invention across a set of cooperating healthcare databases determines the operation of the network for interoperability.

Constructing a Domain

This section will illustrate how a Domain may be constructed and maintained using the invention, making reference to FIGS. 15-18.

Consider a starting state consisting of a number of independent, heterogeneous healthcare Databases. Each Database is associated with a Provider, as in FIG. 15. Users associated with the Provider are authorized to view and edit the data. This association is created through logins, through which Users access a Display connected to the invention, or submit a Batch Load.

Figure 16:
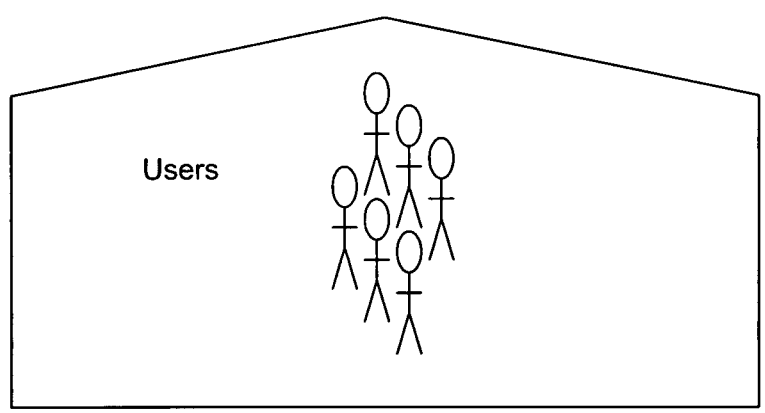
FIG. 16 depicts an example of a Provider with No Associated Databases in accordance with the invention.
Figure 17:
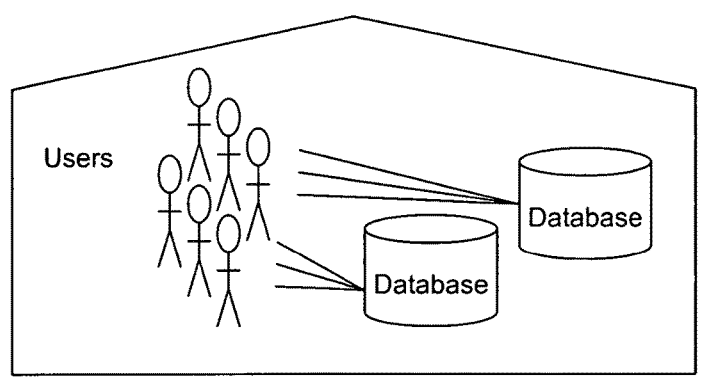
FIG. 17 depicts an example of a Provider Associated with Multiple Databases in accordance with the invention.

It is possible that a Provider is not associated with any Databases, as in FIG. 16, or with more than one, as illustrated in FIG. 17. The former is representative of unautomated healthcare providers, and the latter is representative of large, multi-facility providers with extensive automation.

Each Database may have a system of Person Identifiers assigned to its Individual Persons. Such Databases represent Tier 0 Databases.

To build the Domain, all of the Databases that will be connected are identified. In the starting state, all of the Databases are unrelated, although they are available for connecting via the Internet or other network technology.

Figure 18:
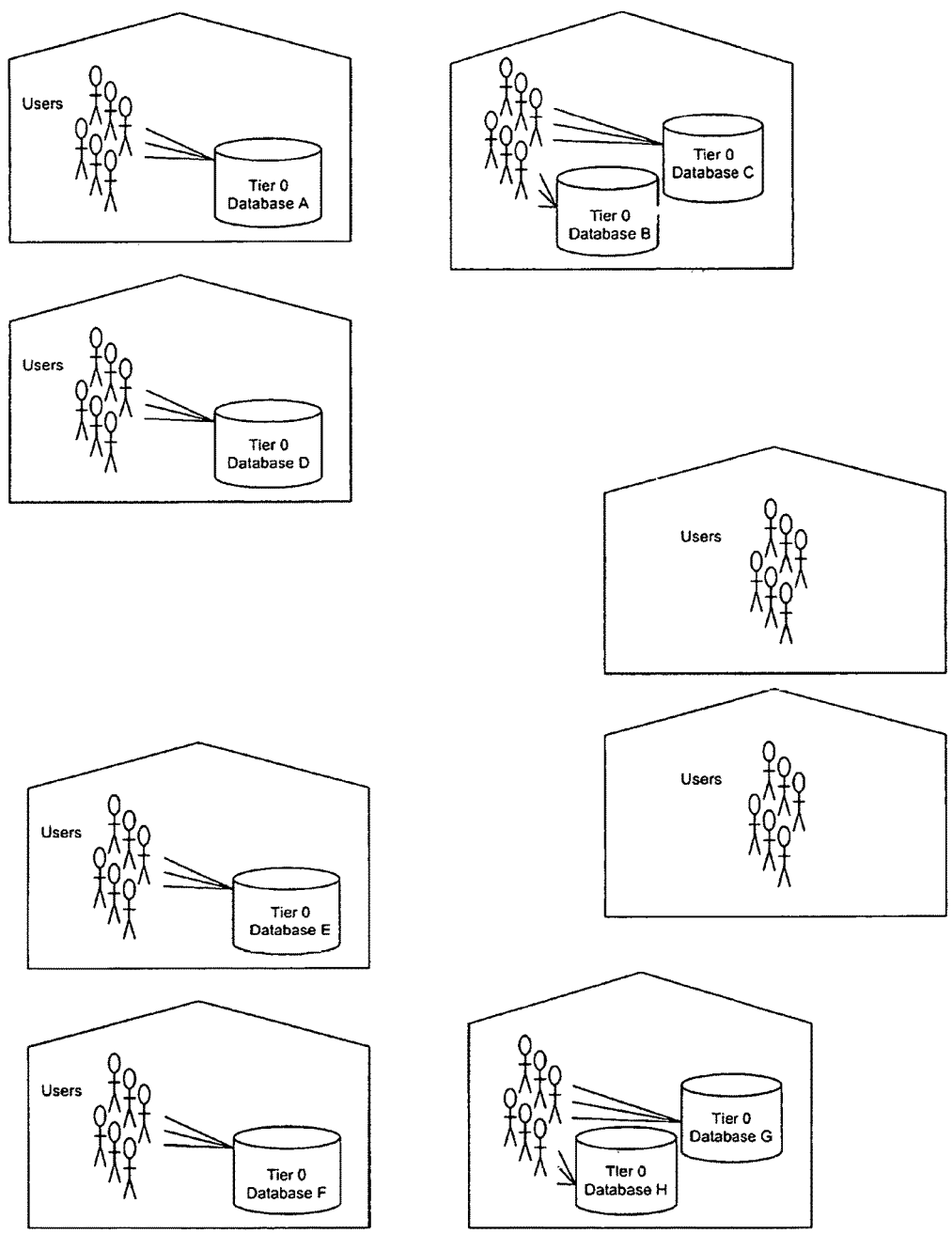
FIG. 18 depicts an example of an initial configuration of Tier 0 Databases in accordance with the invention.

FIG. 18 illustrates an example situation in which some Providers are not associated with any Database, and others with more than one Database. All of the Databases may accordingly be considered Tier 0 Databases.

Creating the Topology

Figure 19:
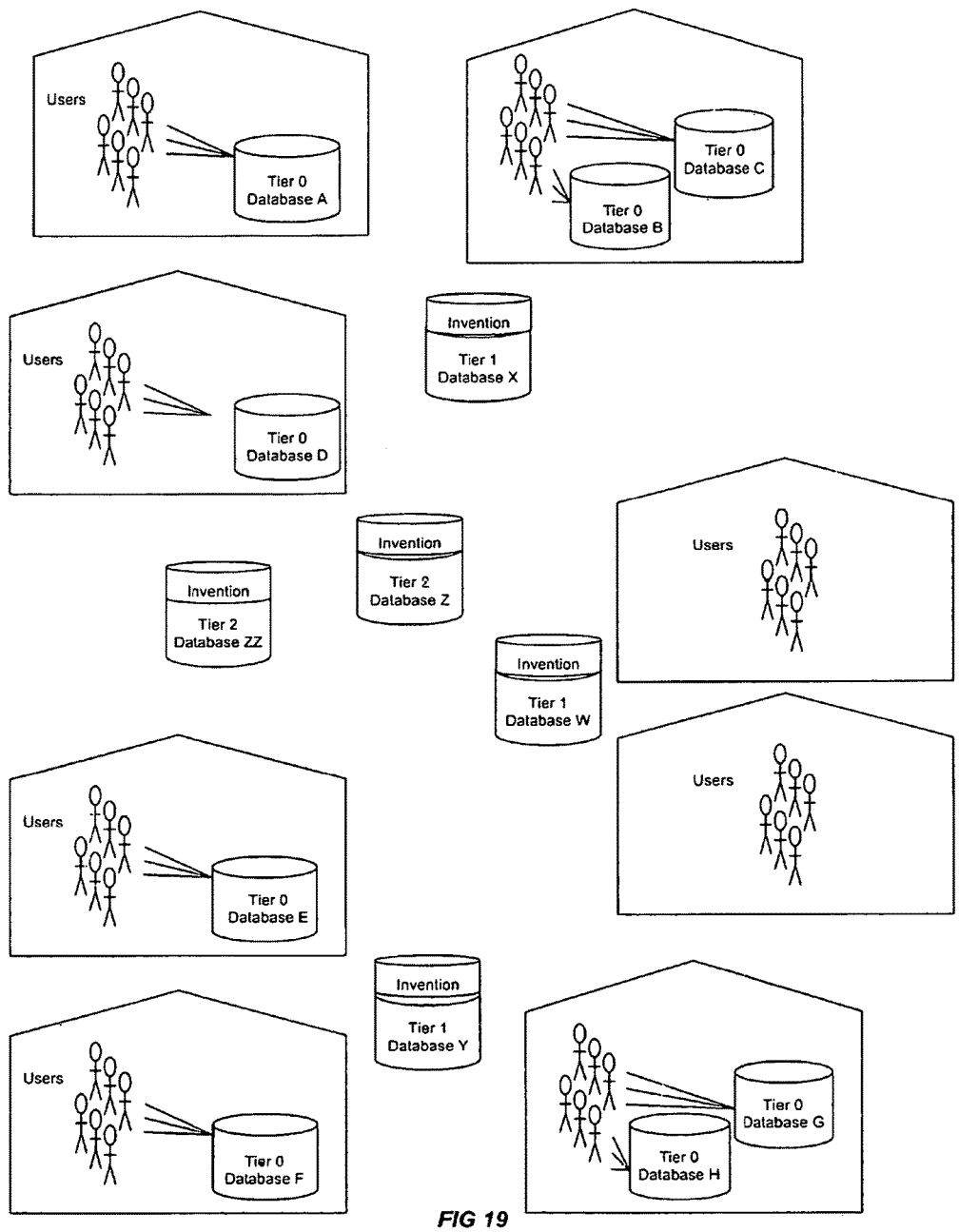
FIG. 19 depicts Databases and Hubs in an example configuration of a Domain in accordance with the invention.

Next, resources are added, as illustrated in FIG. 19. These include Hubs and instances of the invention. The invention is installed and connected to the Hubs.

Optionally, the invention may be installed at Provider locations and connected to Provider Databases. These will be used to implement the Queries and Notifications between the respective Tier 0 Databases and the Hubs.

Relationships

Figure 21:
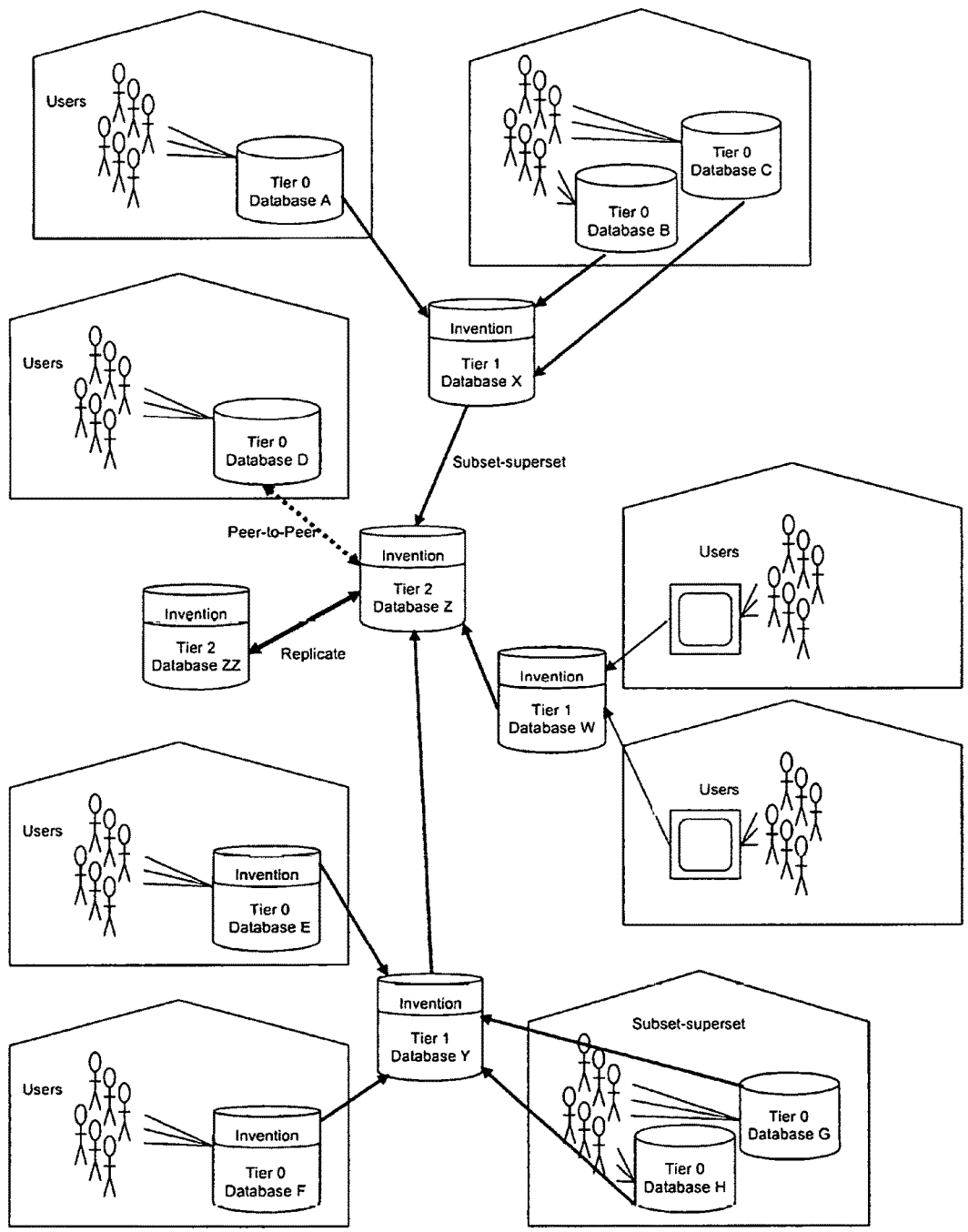
FIG. 21 depicts a Topology generated by an example configuration of a Domain in accordance with the invention.

Next, the instances of the invention in the Domain are configured to produce the desired architecture for interoperability, as illustrated in FIGS. 20-22. Connections are indicated between instances of the invention and:

1. Databases. Each instance of the invention may be related to 1 or more Databases for purposes of reading and writing.
2. Other instances of the invention. The relationships are based upon the sets of Patient Views stored in the Databases associated with each pair. The choices are These relationships are summarized in FIG. 20:
Subset-Superset Relationship
Replicate Relationship
Peer-to-Peer Relationship
3. Displays. Each instance of the invention may be associated with 1 or more Displays for purposes of interfacing with Users who are editing data and who may be resolving indeterminate matches returned by the Matching Algorithm.
4. Other configurable items such as the Service that issues Person Identifiers.

FIG. 21 shows the eventual topology of the example Domain. Connections shown among the Tier 0 Databases and the Hubs and between pairs of Hubs are shown. The corresponding relationships are given in FIG. 22.

Initialization

Figure 23:
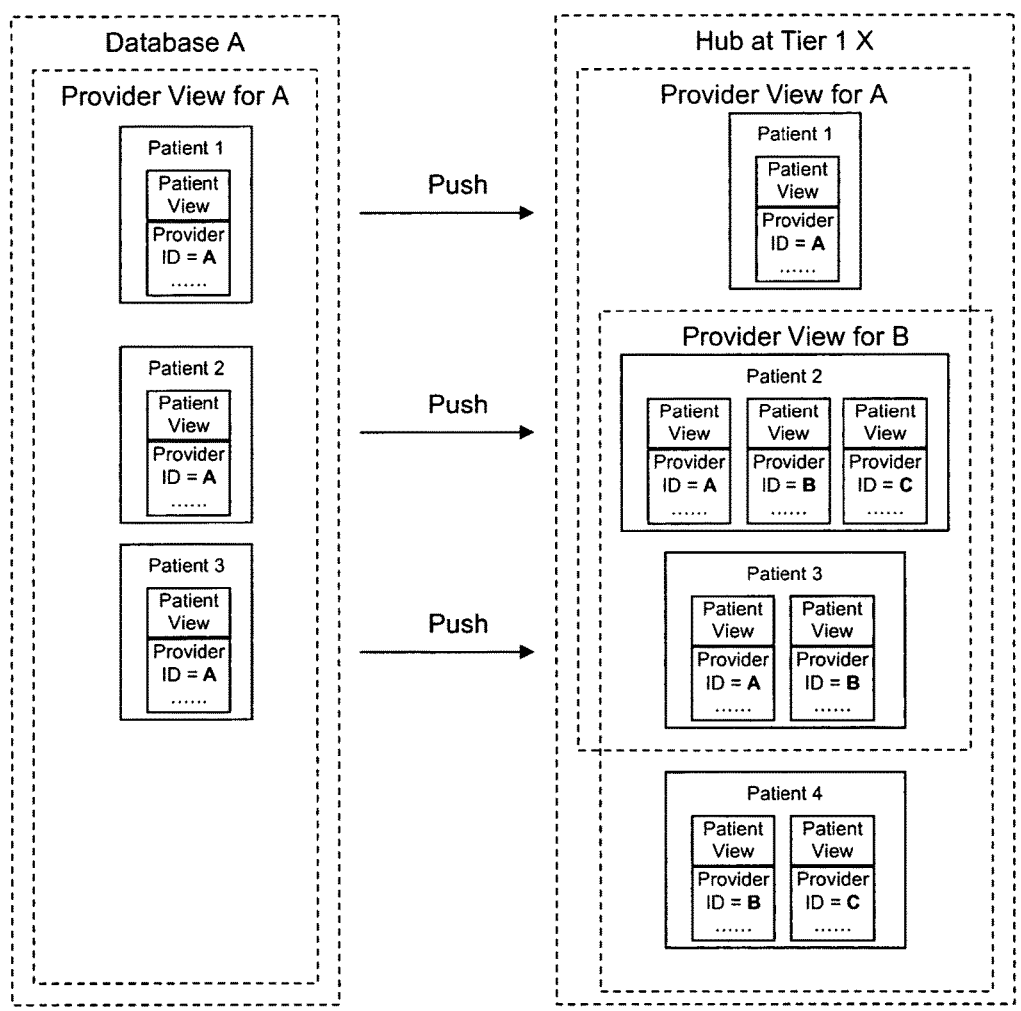
FIG. 23 depicts an example of initializing a Hub in accordance with the invention.
Figure 24:
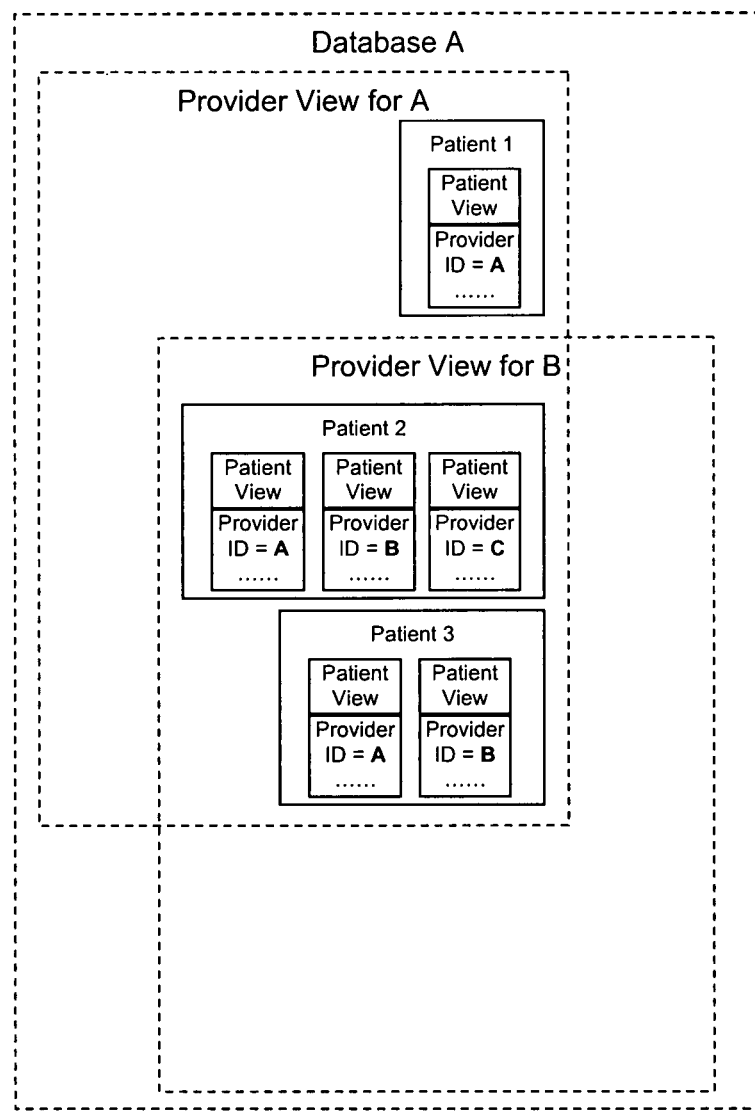
FIG. 24 depicts an Example Provider Database After Initialization in accordance with the invention.

Initialization is illustrated in FIGS. 23 and 24. An initialization process executes Notification Services, or the equivalent, on existing Medical Records to build the shared Patient Views throughout the Domain. Thereafter, Patient Views are maintained in response to edit actions (by Users), which initiate chains of Notifications.

The initialization process includes building the Hubs. This is illustrated in FIG. 23. Recall that some Hubs may contain only MPIs; in this case, only Person Identifiers and Demographic Data may be replicated to the Hub. (Usually the Matching Algorithm uses only Demographic Data, although it is possible to use Clinical Data as well to make a match.)

The Matching Algorithm is executed in creating the Patient Views. Where the Matching Algorithm is unable to decide whether two Patient Views match, the manual verification utility is invoked via the Display and a User must manually resolve the matches.

Note the plurality of Provider Views within the Hub in FIG. 23.

The Domain can also be configured to push data from Hubs back to contributing Provider Databases. Consider the example of FIG. 24, reflecting the state of the Database A after initialization. A in the example is configured to accept Notifications of Patient Views from the Tier 1 X Hub for their common patients. Upon receiving and matching Patient Views from other Databases such as B and C, Tier 1 Hub X is able to determine which are in common with A and forward them.

Query Services

Figure 25:
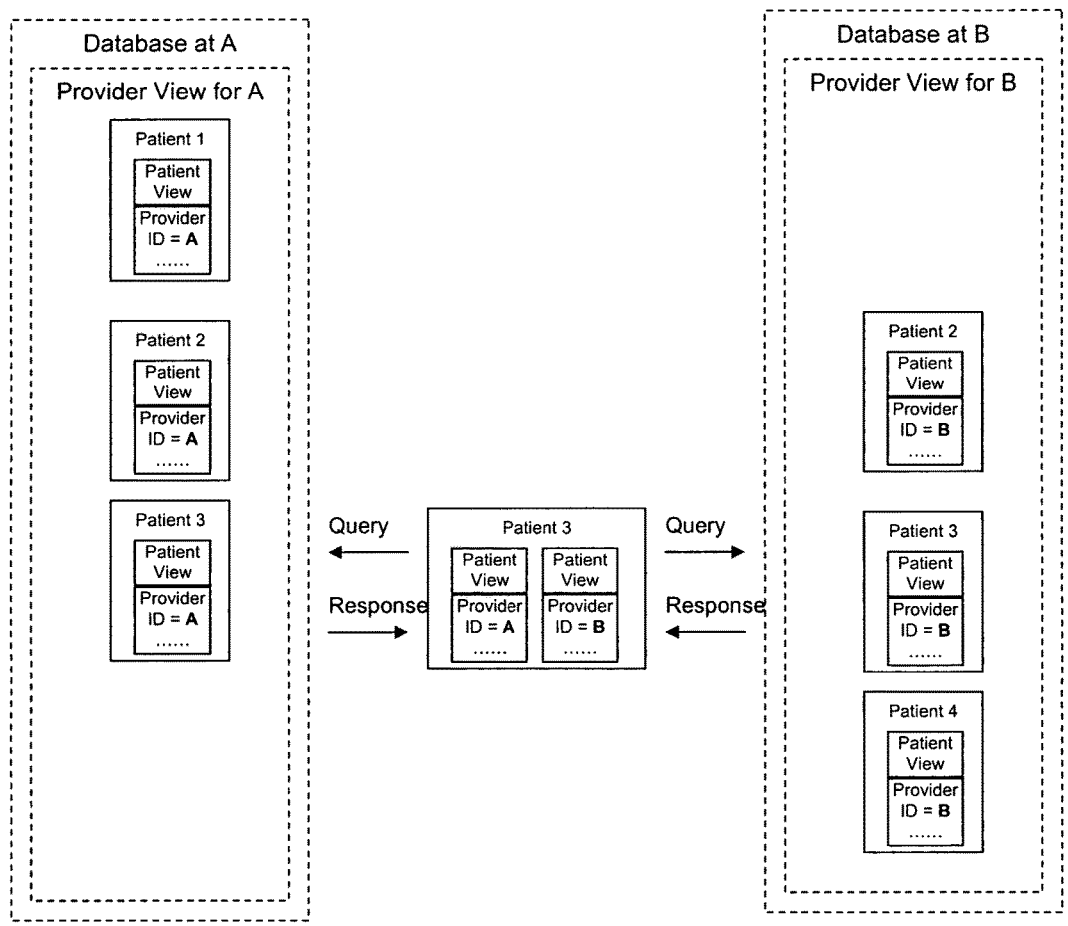
FIG. 25 depicts an example of an Operation of Query Services to Retrieve a Patient View in accordance with the invention.

FIG. 25 illustrates the operation of Query Services to retrieve a Patient View. In most installations, much data throughout the Domain will not be replicated. This is for a variety of reasons: opt-out considerations, competitive considerations, and limits to the practicality of replicating all data. Therefore, often, the Domain will be searched in response to User demand for a particular Patient View. This is accomplished via Query Services.

A Patient View may be assembled on demand, viewed by a User, and discarded. In this case, a search or Query must be executed against each Database that might have a Medical Record participating in the Patient View. The Matching Algorithm must be run against each of these Databases to select the Medical Records for the Individual Person associated with the Patient View. Matching records, if any, are returned.

Query Services may handle this by forwarding Issue Query requests to connected instances of the invention until a match is found, or it can be concluded that none exists. Alternatively, a Patient View may be built in stages. First, Query Services searches the Domain until a match is found in an MPI. Next, Location Data is used by a Filter to retrieve further Medical Data such as Clinical Data and assemble it in a Patient View. Other configurations may also be used.

Related Systems

Some contemporary systems incorporate elements similar to Notifications as described herein, but the Notifications are not practically repeatable. No contemporary system provides an apparatus that enforces the Single Source Rule, and that can be cascaded into a network. Due to the lack of explicit prohibitions to subsequent data editing at the Notification destination in all known systems, repeated, automatic updates produce data inconsistencies and incorrectness that corrupt the participating databases.

An abstraction similar to the Patient View is described in U.S. Pat. No. 6,347,329 to Evans. Evans, however, is concerned with the electronic organization and management of medical data, and lacks features provided in the presently disclosed subject matter.

Similar concepts appear in U.S. Pat. No. 5,560,005 to Hoover. Hoover describes what would currently be referred to as "semantic interoperability"—the mapping of heterogeneous models to a common scheme. Hoover also provides something like an "object broker"—a way to locate and retrieve such data in a network of healthcare systems. Hoover too lacks features provided in the presently disclosed subject matter.

U.S. Pat. No. 5,664,109 to Johnson appears to allow for searches for patient records based upon demographic data, and links related records within a repository. However, Johnson's invention is not suitable for widespread sharing of structured data among multiple providers. Johnson does not provide the cascading that is essential to the configuration of large and complex interoperability networks, as well as other features provided in the presently disclosed subject matter.

U.S. Pat. No. 5,915,240 to Karpf makes use of a concept similar to data replication from a central repository to client databases. However, Karpf also fails to provide for editing restriction based upon provider ownership of data, and hence fails to address the needs of data replication among multiple providers. Karpf also fails to teach any concept of cascading, as well as other features provided in the presently disclosed subject matter.

An article by Gomer Thomas et al. (Gomer Thomas, Glenn R. Thompson, Chin-Wan Chung, Edward Barkmeyer, Fred Carter, Marjorie Templeton, Stephen Fox, Berl Hartman, "Heterogeneous Distributed Database Systems for Production Use. ACM Computing Surveys, Vol. 22, No. 3, September 1990) and Hoover (col. 4 line 51) discuss a sybase replication server, which embodies some principles of Single Source Rule, a definition for which is given above in this disclosure. This concept is believed to be understood by the developers of Sybase Replication Server as the simplest and most effective way of maintaining data correctness across data replication schemes. Sybase Replication Server, however, does not provide an apparatus which automatically enforces these rules. It relies instead upon the software developer to properly design his databases and applications to embody these concepts. It is also invasive, as it works directly off of the DBMS transaction log. Such invasiveness would not be allowed under most current healthcare system security policies today. Sybase Replication Server cannot be practically retrofitted to legacy healthcare applications on a widespread basis, and therefore fails in a number of ways compared to the present disclosure. In addition, Sybase Replication Server lacks many features provided in the presently disclosed subject matter.

Another article ("Application Protocol for Electronic Data Exchange in Healthcare Environments Version 2.5". June, 2003.) refers to Health Level Seven (HL7). The design of HL7 Version 2 and Version 3 reflect the need for both Queries and Notifications by including both types of messages. However, HL7 alone is also not sufficient to solve the objectives of the invention. HL7 contains merely definitions of different types of messages, and lacks many features provided in the presently disclosed subject matter.

A model set forth in Greg W. Donham and Tony Mallia, "The Architecture of the FHIE". Journal of AHIMA/July-August 2006 p. 60-66 describes how the Department of Defense (DoD) and Veterans Administration (VA) use "Domain Relationships" to connect existing healthcare systems. However, this model lacks many features of the presently claimed invention.

In summary, the references discussed above all lack parts of the present invention. Some references incorporate Notifications, but these Notifications are not practically repeatable. Due to possibility of subsequent data editing at the Notification destination, which is not explicitly prohibited, repeated, automatic updates would produce data inconsistencies and incorrectness that would corrupt the system. Also, none of the above references provide an apparatus that can be cascaded. Queries and Notifications can been described over one or two sources and destinations, but do not provide the cascading, with supporting set of features, necessary for the complete configuration of a large and complex network.

The previous description of some aspects is provided to enable any person skilled in the art to make or use the present invention. Various modifications to these aspects will be readily apparent to those skilled in the art, and the generic principles defined herein may be applied to other aspects without departing from the spirit or scope of the invention. For example, one or more elements can be rearranged and/or combined, or additional elements may be added. Thus, the present invention is not intended to be limited to the aspects shown herein but is to be accorded the widest scope consistent with the principles and novel features disclosed herein.

What is claimed is:

1. A method, executing on a plurality of computers, for creating, updating and retrieving patient record replicas on a plurality of destinations, wherein patient record replicas comprise replicas of original patient records, and each original patient record is associated with one patient, and each original patient record is created at one source in a plurality of sources by executing a create operation at the one source, and each original patient record is updated by executing update operations at the one source that created the original patient record, wherein each destination maintains a particular set of provider views, each provider view in the set is associated with a particular source in the plurality of sources, each provider view in the set comprises a set of patient views, wherein each patient view comprises one or more patient record replicas associated with a particular, common patient and at least one patient record replica in each patient view in a particular provider view is associated with the particular source, sources in the plurality of sources grouped into a plurality of sets of sources, for each set of sources in the plurality of sets of sources, at least one destination in the plurality of destinations associated with the set of sources and maintaining the set of provider views wherein one provider view in the set of provider views is associated with each of the sources in set of sources in the plurality of sources, each set of sources in the plurality of sources chosen to produce overlap in the patient views included in the provider views included in the set of provider views maintained by the destination associated with the set of sources destinations grouped into a plurality of aggregated sets of destinations, for each aggregated set of destinations in the plurality of aggregated sets of destinations, at least one destination in the plurality of destinations being associated with the aggregated set of destinations and maintaining the set of provider views wherein one provider view in the set of provider views is associated with each of the sources associated with any provider view maintained by any destination in the aggregated set of destinations, at least one aggregated set of destinations comprising a comprehensive sets of destinations for each comprehensive set of destinations in the plurality of aggregated sets of destinations, at least one provider view maintained by at least one destination in the comprehensive set of destinations in the plurality of aggregated sets of destinations is associated with each source in the plurality of sources, the method comprising:

creating each patient record replica only by replicating a particular create operation and executing the replicated create operation at each destination in the plurality of destinations that maintains the provider view that is associated with the one source in the plurality of sources that executed the particular create operation to create a particular original patient record;

associating the patient record replica with the particular original patient record created by the one create operation;

associating the patient record replica with the source that created the particular original patient record;

updating each patient record replica only by replicating update operations that update the particular original patient record with which the patient record replica is associated and executing the replicated update operations at the destination that created the patient record replica in the order in which the update operations were executed at the source;

each source querying at least one destination in the plurality of destinations associated with the set of sources that includes said source for patient views matching a particular patient, the queried destination returning the patient view matching the particular patient if one exists within any provider view within the set of provider views the queried destination maintains, and if no patient view matching the particular patient is found within any provider view within the set of provider views the queried destination maintains, replicating the query and executing it at at least one destination in at least one aggregated set of destinations maintaining the provider view associated with the querying source the queried destination returning the patient view matching the particular patient if one exists within any provider view within the set of provider views the queried destination maintains, and if no patient view matching the particular patient is found within any provider view within the set of provider views the queried destination maintains, continuing to replicate the query and execute it in succession at destinations in the aggregated set of destinations maintaining the provider view associated with the querying source either until a patient matching the particular patient is found if one exists within any provider view within the set of provider views the queried destination maintains or until at least one destination in the comprehensive set of destinations in the aggregated set of destinations has been queried, the queried destination returning the patient view matching the particular patient if one exists within any provider view within the set of provider views the queried destination maintains.

* * * * *